United States Patent [19]

Anthony

[11] Patent Number: 4,495,360

[45] Date of Patent: Jan. 22, 1985

[54] ULTRAVIOLET LIGHT ABSORBING AGENTS, METHOD FOR MAKING, COMPOSITIONS AND ARTICLES CONTAINING SAME

[75] Inventor: Blair T. Anthony, Schenectady, N.Y.

[73] Assignee: General Electric Company, Schenectady, N.Y.

[21] Appl. No.: 373,361

[22] Filed: Apr. 30, 1982

[51] Int. Cl.$^3$ .............................. C07F 7/08; C07F 7/18
[52] U.S. Cl. .................................... 556/436; 524/266; 428/447; 556/442
[58] Field of Search ................................ 556/436, 442

[56] References Cited

U.S. PATENT DOCUMENTS

| | | | |
|---|---|---|---|
| 3,352,896 | 11/1967 | Dressler et al. | 556/436 |
| 3,395,116 | 7/1968 | Dressler et al. | 556/436 X |
| 4,051,161 | 9/1977 | Proskow | 556/436 |
| 4,277,287 | 7/1981 | Frye. | |
| 4,278,804 | 7/1981 | Ashby et al. | 556/436 |

OTHER PUBLICATIONS

Bazant et al., "Organosilicon Compounds", vol. 1, Academic Press, N.Y. (1965), p. 58.
Noll, "Chemistry and Technology of Silicons", Academic Press, N.Y. (1968), p. 646.

*Primary Examiner*—Paul F. Shaver
*Attorney, Agent, or Firm*—William A. Teoli; James C. Davis, Jr.; James Magee, Jr.

[57] ABSTRACT

A method is provided for making certain methoxy-substituted silyl benzophenones useful as ultraviolet light absorbing agents for silicone hardcoat formulations. The methoxy-substituted benzophenones have been found to more readily equilibrate into silicone hardcoat formulations without adversely affecting the shelf-life of the resulting formulation. The ultraviolet light absorbing agents are obtained by equilibrating a mixture of methanol and trialkoxysilyl-substituted benzophenone in the presence of an acid catalyst. The resulting UV stabilized silicon hardcoat formulations also provide silicone hardcoated plastic articles having improved thermoformability, resistance to abrasion, and environmental degradation.

6 Claims, No Drawings

ULTRAVIOLET LIGHT ABSORBING AGENTS, METHOD FOR MAKING, COMPOSITIONS AND ARTICLES CONTAINING SAME

CROSS REFERENCE TO RELATED APPLICATIONS

References is made to Ser. No. 225,429, filed Jan. 15, 1981 now U.S. Pat. No. 4,436,924, for Bruce Allen Ashby et al, Coating Compositions and Articles Containing the Same, assigned to the same assignee as the present invention.

BACKGROUND OF THE INVENTION

Prior to the present invention, Bruce A. Ashby et al, U.S. Pat. No. 4,278,804, disclosed various ultraviolet light-absorbing agents which were used in silicone harcoats some of which are included by the formula,

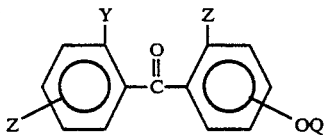

where Y is H or OH, Z is H, OH, OQ or OW, where at least one Z is OH in the ortho position to the carbonyl if Y is H; Q is $-CH_2(CH_2)_nSi(R^1)_x(OR)_y$; and W is $C_mH_{2m+1}$; $x=0$, 1 or 2, $y=1$, 2 or 3, $x+y=3$, $R=$alkyl or alkanoyl having 1 to 6 carbon atoms, $R^1=$alkyl having 1 to 6 carbon atoms, $n=0$, 1 or 2, and $m=1$ to 18.

Some of the silicone hardcoat formulations to which the compositions of formula (1) were employed as ultraviolet light-absorbing agents are shown by Frye, U.S. Pat. No. 4,277,287, assigned to the same assignee as the present invention. These silicone hardcoat formulations comprise the hydrolysis product of an aqueous dispersion of colloidal silica and an organotrialkoxysilane of the formula,

$$R^2Si(OR^3)_3 \qquad (2)$$

where $R^2$ is alkyl having 1-3 carbon atoms, or aryl having $C_{(6-13)}$ carbon atoms, and $R^3$ is $C_{(1-8)}$ alkyl.

Although valuable results were achieved by using the ultraviolet light-absorbing agents of formula (1) in silicone hardcoat formulations resulting from the employment of organotrialkoxysilane of formula (2), the "age-in" time required for cohydrolyzing the UV light-absorbing agents under ambient conditions into the silicone hardcoat formulation, often required 4–6 weeks. As a result, the weight percent of the ultraviolet light-absorbing agent actually equilibrated into the silicone hardcoat formulation was often insufficient to impart a satisfactory degree of weatherability resistance and thermoformability to thermoplastic substrates, such as polycarbonate sheets treated with such UV-stabilized silicone hardcoat formulation and thereafter cured.

As used hereinafter, the term "age-in" means the time required for ultraviolet light absorbing agent utilized in the practice of the invention, or as shown by formula (1) to be sufficiently equilibrated into the silicone hardcoat formulation to produce a desirable coating. For example, an ultraviolet light-absorbing agent of formula (1) would be sufficiently aged-in, or equilibrated into the silicon hardcoat formulation, if the UV-stabilized silicone hardcoat formulation resulting from the incorporation of the ultraviolet light-absorbing agent after the age-in period could be coated onto a transparent thermoplastic test panel, for example, a polycarbonate test panel, to produce a crack-free clear film after a 30 minute air dry and a cure for 90 minutes at 135° C.

Improved age-in performance of ultraviolet light-absorbing agents into silicone hardcoat formulations has been found if ultraviolet light-absorbing agents having the formula,

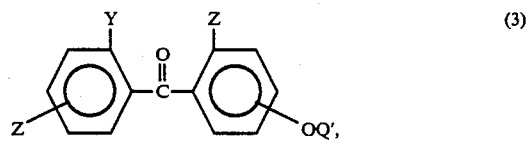

are used, where Y and Z are as previously defined, Q' has the formula,

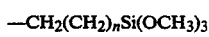

$$-CH_2(CH_2)_nSi(OCH_3)_3$$

and n is as previously defined in formula (1).

It also has been found that ultraviolet light-absorbing agent of formula (3), having trimethoxy substitution on the silicon atom can be cohydrolyzed at ambient temperatures into silicon hardcoat formulation within a week. In addition to having superior age-in time, the weight percent of the cohydrolyzed trimethoxysilyl substituted benzophenone can exceed 25% by weight of the total solids in the silicone hardcoat formulation. Accordingly, the weatherability and thermoformability of cured silicone hardcoats on thermoplastic substrates containing ultraviolet light absorbing agents of formula (3) can be substantially enhanced. However, experience has also shown that the employment of ultraviolet light-absorbing agents of formula (3) having trimethoxysilylalkyl substitution often result in silicone hardcoat formulations which prematurely gel, and therefore are rendered useless for silicone hardcoat applications because the ultraviolet light stabilized silicone hardcoat formulation does not have sufficient shelf life.

Prior to the present invention, methods available for making ultraviolet light-absorbing agents of formula (3), substituted with trimethoxysilylalkyl groups, as shown above, were generally limited to procedures utilizing trimethoxysilane which is known for its extreme toxicity. For example, trimethoxysilane can be added to an allyloxy derivative of hydroxybenzophenone via a hydrosilation reaction to produce an ultraviolet light-absorbing agent within the scope of formula (3). However, this platinum catalyzed addition of such silicon hydride would not be feasible in large scale production due to the toxicity problem previously discussed. It would therefore be desirable to develop a method for producing an ultraviolet light-absorbing agent for silicone hardcoat formulations which would have a reduced age-in time in the silicone hardcoat formulation without resulting in premature gelation and which would be based on procedures which could be utilized in large scale operations without any danger of toxicity.

The present invention is based on my discovery that ultraviolet light-absorbing agents of the formula

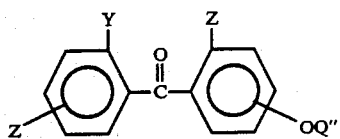

where Q'' is

Z, Y, R and n are as previously defined and "a" has an average value of from about 0.5 to about 2.5 inclusive, camn be made readily to provide UV stabilized silicone hardcoat formulations having improved age-in time without suffering from premature gelation time during the shelf period. The methoxy-alkoxysilylalkyl-substituted benzophenones of formula (4), where R is preferably $C_2H_5$, do not require the use of trimethoxysilane, but can be readily synthesized by equilibrating an ethoxysilyl alkyl-substituted benzophenone within the scope of formula (1) with methanol in the presence of an effective amount of an acid catalyst.

STATEMENT OF THE INVENTION

A method which comprises, equilibrating a mixture of about 0.6 to 9 moles of methanol, per mole of trialkoxysilylalkyl ultraviolet light-absorbing agent having the formula,

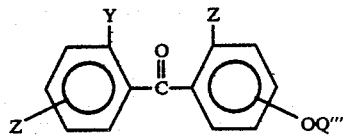

where Q''' is

and Y, Z, R and n are as previously defined, in the presence of an acid catalyst to produce a methoxyalkoxysilylalkyl ultraviolet light-absorbing agent of formula (4), which has reduced age-in time in silicone hardcoat formulations without producing UV stabilized silicone hardcoat formulations suffering from premature gelation at ambient temperatures and where the resulting UV stabilized silicone hardcoat formulation can be applied to primed or unprimed organic polymeric thermoplastic substrates to produce composites upon cure of the UV stabilized silicone hardcoat formulation exhibiting improved weatherability and thermoformability.

An alternate procedure which can be used to make the methoxy-alkoxy ultraviolet light absorbing agents of formula (4) is to add a trihalosilane onto an alkeneoxy-substituted benzophenone by a hydrosilation reaction and thereafter effecting reaction between the resulting trihalosilylalkyl benzophenone with a mixture of methanol and alkanol, for example, ethanol, in suitable proportions.

Some of the methoxy-alkoxysilylalkyl ultraviolet light-absorbing agents which can be used in the practice of the present invention shown by formula (4) are as follows:

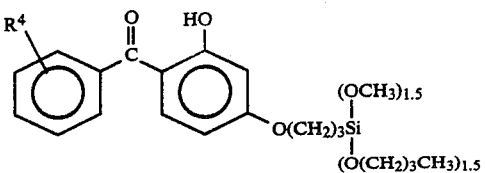

where $R^4$ is H, or $CH_3$,

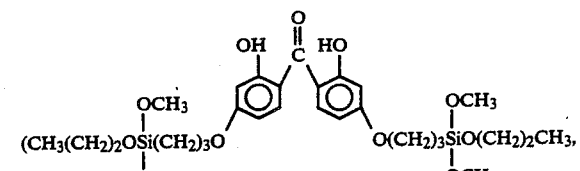

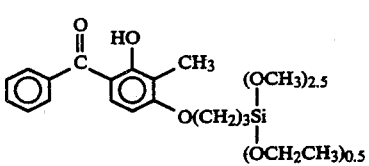

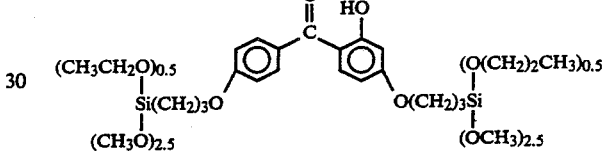

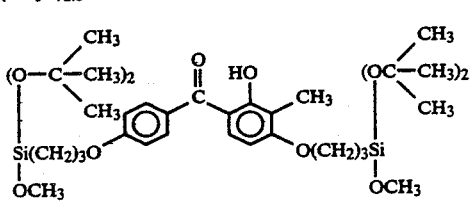

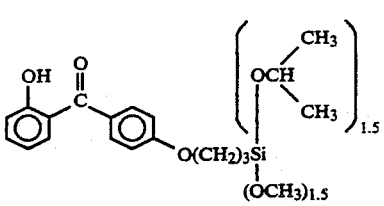

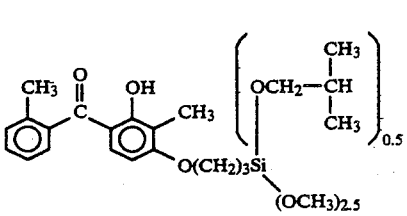

The UV-stabilized silicone hardcoat formulations of the present invention can be made by adding an effective amount of the methoxy-alkoxysilylalkyl UV-absorbing agents of formula (4) to silicone hardcoat formulations, for example, as shown in the above U.S. Pat. No. 4,277,877 to Frye, assigned to the same assignee as the present invention.

In general, the aqueous dispersion of colloidal silica utilized in the silicone hardcoat formulations which can be used in the practice of the present invention is characterized by a particle size of from 5 to 150 millimicrons, and preferably from 10 to 30 millimicrons average diameter. Such dispersions are known in the art. Commercially available materials include Ludox (Dupont) and Nalcoag (NALCO Chemical Co.). These are available in the form of acidic or basic hydrosols. With regard to this invention, if the pH of the coating composition is basic, then usually a basic colloidal silica sol is preferred for use in the composition. On the other hand, colloidal silicas which are initially acidic, but which have been adjusted to the basic can also be used. It has been found that colloidal silica having a low alkali content, e.g., less than 0.35% by weight as $Na_2O$, provides a more stable coating composition, and these are preferred.

In preparing the formulations, the aqueous dispersion of colloidal silica is added to a solution of a small amount, e.g., from 0.07 to 0.10 percent by weight, of an alkyltriacetoxysilane, alkyltrialkoxysilane, or aryltrialkoxysilane. The temperature of the reaction mixture is kept in the range between 20° C. to 40° C., preferably below 25° C. A reaction time of about six to eight hours is usually sufficient to react enough of the trialkoxysilane such that the initial two-phase liquid mixture has been converted to a single liquid phase in which the silica is dispersed. Hydrolysis is permitted to continue for a period of 24 to 48 hours, depending on the desired final viscosity. As a rule, the longer the time permitted for hydrolysis, the higher the final viscosity.

During the preparation of the coating formulations, the alkyltriacetoxysilane is employed to buffer the viscosity of the initial two-phase liquid reaction mixture, and also to regulate the hydrolysis rate. Preferred are those alkyltriacetoxysilanes in which the alkyl group contains from 1 to 5 carbon atoms, and especially 1 to 3 carbon atoms. Methyltriacetoxysilane is the most preferred. Although alkyltriacetoxysilanes are preferred for use, it is to be understood that glacial acetic acid or other acids may be used instead. Such other acids include organic acids, such as propionic butyric, citric, benzoic, formic, oxalic, and the like. After hydrolysis has been completed, the solids content of the coating composition is adjusted by adding alcohol to the reaction mixture. Suitable alcohols include lower aliphatics, e.g., having 1 to 6 carbon atoms, such as methanol, ethanol, propanol, isopropanol, n-butyl alcohol, t-butyl alcohol, and the like, or mixtures thereof. Isopropanol is preferred. The solvent system, i.e., mixture of water and alcohol, should contain from about 20 to 75 percent by weight of the alcohol to ensure that the partial siloxanol condensate is soluble.

Optionally, additional water-miscible polar solents, e.g., acetone, butyl cellosolve, or the like, can be included in minor amounts, usually no more than 20 percent by weight of the solvent system.

After adjustment with solvent, the coating composition preferably has a solids content of from about 18 to about 25% by weight, especially preferably about 20% by weight of the total composition.

The coating composition has a pH of from about 3.5 to about 8, preferably, from about 7.1 to about 7.8, and especially preferably about 7.2 to about 7.8. If necessary, a base, such as dilute ammonium hydroxide, or weak acid, such as acetic acid, is added to adjust the pH within this range.

The silanetriols, $R^2Si(OH)_3$, are formed in situ as a result of admixing the corresponding trialkoxysilanes with the aqueous medium, i.e., the aqueous dispersion of colloidal silica. Examples of the trialkoxysilanes are those containing methoxy, ethoxy, isopropoxy and n-butoxy substituents which, upon hydrolysis, generate the silanetriols and further liberate the corresponding alcohol, e.g., methanol, ethanol, isopropanol, n-butanol, and the like. In this way, at least a portion of the alcohol content present in the final coating formulation is provided. Upon generating the hydroxyl substituents to form

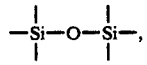

bonding occurs. This condensation, which takes place over a period of time, is not exhaustive but rather the siloxane retains a quantity of silicon-bonded hydroxyl groups which render the polymer soluble in the alcohol-water solvent mixture. This soluble partial condensate can be characterized as a siloxanol polymer having at least one silicon-bonded hydroxyl group for every three

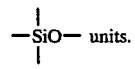

The portion of the coating formulation which consists of non-volatile solids is a mixture of colloidal silica and the partial condensate (or siloxanol) of a silanol. The major portion of all of the partial condensate or siloxanol is obtained from the condensation of $CH_3Si(OH)_3$. Depending on the input of ingredients to the hydrolysis reaction, minor amounts of partial condensate can be obtained, e.g., such as from the condensation of $CH_3Si(OH)_3$ with $C_2H_5Si(OH)_3$ or $C_3H_7Si(OH)_3$, of $CH_3Si(OH)_3$ with $C_6H_5Si(OH)_3$, or mixtures of the foregoing. For best results, it is preferred to use only methyltrimethoxysilane (thus generating all mono-methylsilanetriol) in preparing the coating compositions. In the preferred embodiments, the partial condensate is present in an amount of from about 55 to 75 percent by weight, (the colloidal silica being present in an amount of from about 25 to about 45% by weight) based on the total weight of solids in the solvent comprising a mixture of alcohol and water. The alcohol comprises from about 50% to 95% by weight of the solvent mixture.

The coating formulations completely cure to hard coatings at a temperature of about 120° C., without the necessity of a curing catalyst. If milder curing conditions are desired, it is preferred to include a buffered latent condensation catalyst. Such catalysts are known to those skilled in the art. Examples include alkali metal salts of carboxylic acids, such as sodium acetate, potassium formate, and the like, amine carboxylates, such as dimethylamine acetate, ethanolamine acetate, dimethylaniline formate, and the like; quaternary ammonium carboxylates, such as tetramethylammonium acetate, benzltrimethylammonium acetate, and the like; metal carboxylates, such as tin octoate; amines, such as triethylamine, triethanolamine, pyridine, and the like; and alkali hydroxides, such as sodium hydroxide, ammonium hydroxide, and the like. It should be noted that commercially available colloidal silicas, particularly those having a basic pH, i.e., above 7, contain free alkali metal base, and alkali metal carboxylate catalysts are generated in situ during hydrolysis.

The amount of the curing catalyst can vary widely, depending upon particular requirements. In general, the catalyst is present in an amount of from about 0.05 to about 0.5 and preferably about 0.1 percent by weight of the total coating composition. Such compositions are curable on the substrate within a brief period of time, e.g., from 30 to 60 minutes, using temperatures in the range from about 85° to about 120° C. A transparent, abrasion-resistant coating results.

The ultraviolet light-absorbing agents of formula (4) are added to the described silicone hardcoat formulation before, during and after hydrolysis, and also before or after addition of solvent to adjust the solids. The ultraviolet light absorbing agent of formula (4) can be added to the silicone hardcoat composition as the equilibrated reaction mixture or as a methoxyalkoxysilylalkyl benzophenone within the scope of formula (4) substantially free of methanol, alkanol or mixtures thereof. In preferred compositions, the ultraviolet light absorbing agents of this invention are used in amounts of from about 1.0 to about 40.0, preferably from 5.0 to 20.0 parts by weight per 100 parts by weight of the resulting UV-stabilized silicone hardcoat formulation on a basis of solids.

Other ingredients may also be added. Special mention is made to polysiloxane-polyether copolymers, which control flow and prevent flow marks, dirt marks, and the like, on the coating surface. Such materials also increase the stress cracking resistance of the coating.

Preferred for use in this invention are liquid polysiloxane-polyether copolymers having the following formula:

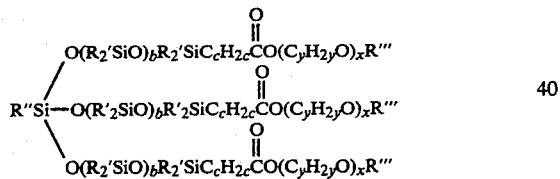

wherein R' and R" are monovalent hydrocarbons, R''' is lower alkyl, preferably alkyl having 1 to 7 carbon atoms, b is at least 2, preferably 2 to about 40, c is from 2 to 3, y is from 2 to 4, and x is at least 5, preferably 5 to 100.

By way of illustration, R' and R", independently, are alkyl, such as methyl, ethyl, propyl, butyl, octyl, and the like; cycloalkyl, such as cyclohexyl, cycloheptyl, and the like; aryl, such as phenyl, tolyl, naphthyl, xylyl, and the like; aralkyl, such as benzyl, phenylethyl, and the like; alkenyl or cycloalkenyl, such as vinyl, allyl, cyclohexenyl, and the like; and halogenated derivatives of any of the foregoing, such as chloromethyl, chlorophenyl, dibromophenyl, and the like. Illustratively, R''' is methyl, ethyl, propyl, butyl, isobutyl, amyl, and the like.

The preparation of the above polysiloxanepolyether copolymer is described in U.S. Pat. No. 3,629,165, incorporated herein by reference. Suitable commercially available materials are SF-1066 and SF-1141, from General Electric Company, Mallinckrodt's BYK-300, Union Carbide's L-540 and Dow-Corning's DC-190.

Other ingredients, such as thickening agents, pigments, dyes, antioxidants and the like, can also be included for their conventionally employed purposes. These can be added to the compositions after hydrolysis has been completed.

The antioxidants can be used in the UV stabilized silicone hardcoat formulation in a proportion of from 0.1 to 2 parts and preferably 0.5 to 1 part, per 100 parts of the UV stabilized silicone hardcoat composition. Some of the antioxidants which can be used in the practice of the invention are materials manufactured by the Ciba Geigy Company of Ardsley, N.Y. and are as follows:

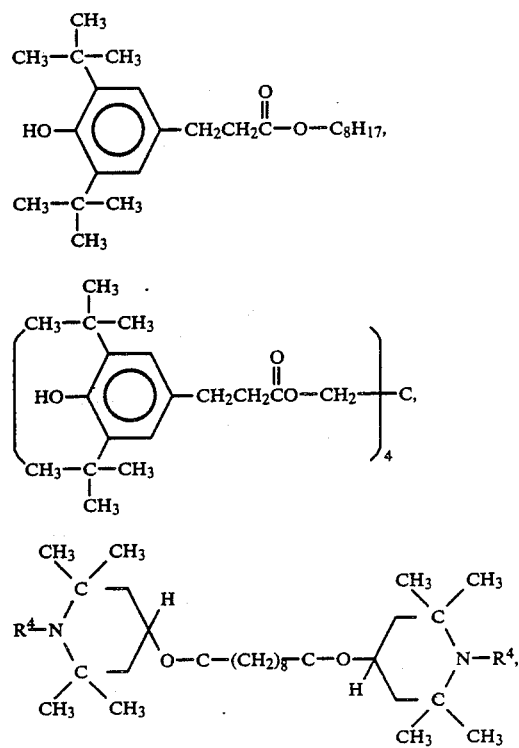

where $R^4$ is as previously defined,

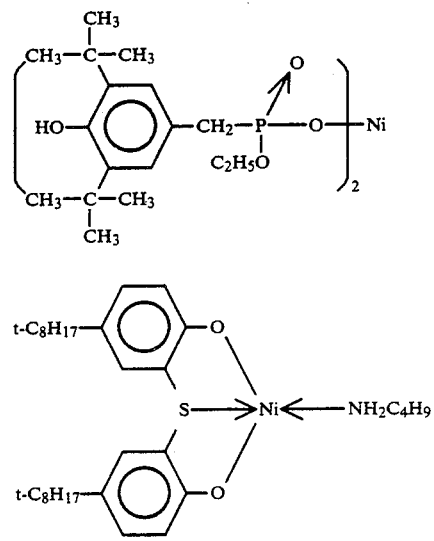

[2,2'-Thiobis(4-t-octylphenolato)]-n-butylamine Nickel-(II)

The coating formulations can be applied to the surface of an article after priming, e.g., with a thermosetting acrylic, using conventional methods, eg., as by flow coating, spraying or dip coating, to form a continuous film or layer thereon. The cured compositions are useful as protective coatings on a wide variety of surfaces, either transparent or opaque, including plastic surfaces and metal surfaces. Examples of such plastics include synthetic organic polymeric substrates, such as acrylic polymers, e.g., poly(methylmethacrylate), and the like; polyesters, eg., poly(ethylene terephthalate), poly(butylene terephthalate), and the like; polyamides, polyimides, acrylonitrile-styrene copolymers; styreneacrylonitrile-butadieneterpolymers; polyvinyl chloride; butyrates, polyethylene, and the like.

Special mention is made of the polycarbonates, such as those polycarbonates known as Lexan ® polycarbonate, available from General Electric company, including transparent panels made of such materials. The compositions of this invention are especially useful as protective coatings on the primed surfaces of such articles.

Suitable substrates also include both bright and dull metal surfaces, such as aluminum or sputtered chromium alloys. In addition, the coating compositions of this invention can be applied on other types of surfaces such as wood, leather, glass, ceramics, textiles, and the like.

A silicone hardcoat is obtained by removing the solvent and other volatile materials from the composition. The coating air-dries to a substantially tack-free condition, but heating in the range of 75° C. to 200° C., is necessary to obtain condensation of residual silanols in the partial condensate. Final cure results in the formation of silsesquioxane ($R^2SiO_{3/2}$). In the cured coating, the ratio of $R^2SiO_{3/2}$ to $SiO_2$, where $R^2$ is methyl, equal to 2, is most preferred. The coating thickness can be varied, but in general, the coating will have a thickness in the range between 0.5 to 20 microns, more usually from 2 to 10 microns.

In order that those skilled in the art will be better able to practice the invention, the following examples are given by way of illustration and not by way of limitation. All parts are by weight.

EXAMPLE 1

There was prepared 4-[γ(triethoxysilyl)propoxy]-2-hydroxybenzophenone by adding 10 drops of a 5% platinum-vinyl-siloxane complex hydrosilation catalyst under nitrogen with stirring to a mixture of 5.08 gram of 4-allyloxy-2-hydroxybenzophenone The solution becomes warm and the reaction is completed in 1½ hour. Evaporation of the solvent at 50° C. under a vacuum leaves a light-yellow viscous oil containing traces of dark particles which are removed by filtration. Based on the procedure shown in U.S. Pat. No. 4,278,804 and elemental analysis, there was obtained 4-[γ(triethoxysilyl)propoxy]-2-hydroxybenzophenone.

There was introduced into a mixture of 19 grams of the above triethoxysilylbenzophenone and 100 grams of anhydrous methanol, 30 bubbles of gaseous HCl. The resulting mixture was heated at 50° C. for 1.5 hours. Based on method of preparation, there was obtained, after the solvent was stripped, a quantitative yield of a 2-4-hydroxy-4-(γ-methoxy-ethoxysilane)propoxybenzophenone having the following average formula,

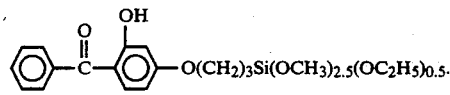

The identity of the product was further confirmed by NMR and LC analyses which showed a mixture of the trimethoxy, dimethoxy-ethoxy and methoxydiethoxy.

There was added 3.2 parts of the above methoxy-ethoxysilylpropylbenzophenone to 100 parts of a silicone hardcoat formulation to produce a UV stabilized silicone hard coat formulation. The silicone hardcoat formulation was prepared as follows:

Twenty-two and one-tenths parts by weight of Ludox LS silica Sol (DuPont, an aqueous dispersion of colloidal silica having an average particle size of 12 millimicrons and a ph of 8.4), is added to a solution of 0.1 part by weight of methyltriacetoxysilane in 26.8 parts by weight of methyltrimethoxysilane. The temperature of the reaction mixture is kept at 20° C. to 25° C. The hydrolysis is allowed to continue for 24 hours. Five parts by weight of a poluysiloxane-polyether copolymer (SF-1066 General Electric Company) is introduced as a flow control agent. The resulting reaction mixture has a solids content of 40.5%. Isobutanol is added to bring the solids content to 20%. The pH of the composition is about 7.2.

After the above methoxy-ethoxysilylpropylbenzophenone was allowed to equilibrate or "age-in" into the silicone hardcoat formulation for 48 hours at ambient temperatures, it was flow coated onto a transparent Lexan polycarbonate panel by dipping the panel into the UV stabilized silicone hardcoat formulation and allowing it to air dry.

The above procedure was repeated, except that 3.2 grams of 4-[γ(triethoxysilyl)propoxy]-2-hydroxybenzophenone was substituted for the methoxy-ethoxysilylpropylbenzophenone in 100 parts of the silicone hardcoat formulation. Again, a Lexan polycarbonate panel was flow coated with the resulting silicon hardcoat composition and allowed to air dry.

A third UV-stabilized silicone hardcoat formulation was made, using the above-mentioned silicone hardcoat formulation and a UV stabilizer 4-[γ(trimethoxysilyl)-propoxy]-2-hydroxybenzophenone following the same procedure as above. The various UV-stabilized silicone hardcoat formulations were also flow coated onto Lexan polycarbonate panels and allowed to air dry.

In addition to being flow coated onto Lexan polycarbonate panels and allowed to air dry, portions of the respective UV-stabilized silicone hardcoat formulations were placed in capped vials and allowed to shelf age for a period of at least 7 days at ambient temperatures.

The following results were obtained from the above-described UV-stabilized hardcoat formulations, where "UV stabilizer" means the particular silylalkyl benzophenone UV stabilizer used in the silicone hardcoat formulation, "48 Hour Age-in Coating" means the nature of the coating on the transparent polycarbonate panel obtained by allowing the UV stabilized hardcoat formulation to air-dry, and "Gel" means whether gellation occurred in the capped vials after the above shelf period as shown by the separation of gel particles:

TABLE I

| UV Stabilizer | 48 Hour Age-In Coating | Gel Time (days) |
| --- | --- | --- |
| methoxy-ethoxy | clear | >45 |
| triethoxy | hazy | 120–180 |
| trimethoxy | clear | 7–14 |

The above results show that silicone hardcoat formulations of the present invention containing the methoxy-ethoxysilylpropylbenzophenone UV stabilizer of formula (4) are superior with respect to age-in time and shelf stability, to UV stabilized hardcoat formulations of the prior art containing the triethoxy or trimethoxysilyl-propylbenzophenone UV stabilizers. In addition, substantially equivalent UV stabilized hardcoat formulations were obtained when methoxy-ethoxysilylpropyl-benzophenone stabilizers were used where "a" in formula (4) varied from 0.5 to 2.5.

EXAMPLE 2

There is prepared 4-[γ-(trimethoxysilyl)propoxy]-2-hydroxybenzophenone by adding 10 drops of a 5% platinum vinyl-siloxane complex hydrosilation catalyst under nitrogen with stirring to a mixture of 25.4 parts of 4-allyloxy-2-hydroxybenzophenone in 12.2 grams of trimethoxysilane in 100 ml of dry toluene. The solution becomes warm and the reaction is completed in ½ hour. Evaporation of the solvent at 50° C. under a vacuum leaves a light-yellow viscous oil containing traces of dark particles which are removed by filtration. There is obtained a film of 37.5 grams of 4-[γ(trimethoxysilyl)-propoxy]-2-hydroxybenzophenone. The identity of the product is further confirmed by NMR and carbon-hydrogen analysis.

Several methoxy-ethoxysilylpropoxy-2-hydroxybenzophenones within the scope of formula (4) were prepared by equilibrating various mixtures of methanol and 4-[γ(triethoxysilyl)propoxy]-2-hydroxybenzophenone. The mixtures were prepared by separately equilibrating 19 parts of 4-[γ-(triethoxysilyl)propoxy]-2-hydroxybenzophenone with various amounts of methanol. The various mixtures were equilibrated for 15 minutes, at a temperature of 50° C. in the presence of 0.5% by weight of anhydrous HCl, based on the weight of the equilibration mixture. The methoxy-ethoxysilylpropylbenzophenone UV-stabilizers obtained were within the scope of formula (4), where "a" in Table II corresponds to the value of "a" in formula (4) and "methanol" shows the grams of methanol used, per 19 grams of the 4-[γ(triethoxysilyl)propoxy]-2-hydroxybenzophenone in the equilibration mixture:

TABLE II

| "a" | Methanol |
| --- | --- |
| 0.5 | >50 |
| 1.5 | 4 |
| 2.5 | 1 |

Several UV-stabilized silicone hardcoat formulations were prepared utilizing the above-described methoxy-ethoxysilylpropylbenzophenone UV-absorbers with the above-described silicone hardcoat formulation at 16% by weight, based on the weight of solids in the UV stabilized silicone hardcoat formulation.

After a sufficient age-in period, the various UV-stabilized silicone hardcoat formulations were then used to treat ⅛ inch×4 inch×4 inch polycarbonate test panels. The respective coated polycarbonate panels were then placed in an oven at 135° C. for 90 minutes and removed thereafter from the oven. The panels were then tested for adhesion and "Taber Hardness".

Adhesion was determined by the cross-hatch method (ASTM-3359). The coated Lexan polycarbonate panel was cut with a lattice cutting tester (Erichsen, Germany) and test with adhesive tape (Scotch 710). Three tape pulls were done on scribed area and only 100% adhesion was considered as "pass". A standard Taber Abrasion Tester, model 174 was used with freshly sanded wheels. The haze was measured by Gardner Haze Meter model UX10.

The following results were obtained, where the Taber Abrasion Tester was run for 300 cycles, "Silane Ethoxy Value" shows the value of "a" of the UV stabilizer of formula (4), and "Shelf Life" shows the time in days that the UV-stabilized silicone hardcoat formulation was free of gel formation under ambient conditions and "Adhesion" indicates whether the adhesion test was passed or failed:

TABLE III

| Silane Ethoxy Value | Age-in Time (days) | Adhesion | Haze (%) | Shelf Life (days) |
| --- | --- | --- | --- | --- |
| 0 | 2 | passed | 7.4 | 7–14 |
| 0.5 | 2 | passed | 5.5 | >45 |
| 1.5 | 2 | passed | 6.5 | >60 |
| 2.5 | 3 | passed | 11.3 | >90 |
| 3 | 6 weeks | passed | 5–9 | 120–180 |

The above results show that the methoxyalkoxysilyalkyl-substituted benzophenones of the present invention, as shown by formula (4), which include silanes having a silane ethoxy value of 0.5 to 2.5, provide superior UV-stabilized silicone hardcoat formulations as compared to the ultraviolet light-absorbing agents of the prior art, where "a" has a value of 0 or 3.

EXAMPLE 3

A UV-stabilized silicone hardcoat formulation was prepared utilizing the silicone hardcoat formulation of Example 1 and a UV stabilizer of Example 2, at 16% by weight based on the weight of solids in the resulting UV stabilized hardcoat formulation having an "a" value of 0.5. Several polycarbonate test panels were then treated with the UV-stabilized silicone hardcoat formulation and flow coated onto the test panels. The panels were then air dried for 30 minutes and then cured for 1½ hour at 135° C.

Some of the treated polycarbonate test panels were tested in a QUV device, manufactured by the Q-Panel company of Cleveland, Ohio. The device can be set to consecutive cycles of fluorescent UV light and high humidity at various times and temperatures. After QUV exposure the panels can then be subjected to an adhesion test as described above.

Some of the panels also were subjected to a "Water Soak Test" by submersing them in a deionized water bath maintained a 65° C. The resulting panels were checked daily for adhesion as described above.

Additional coated panels were subjected to the Humidity Oven Test, where the coated polycarbonate panels were placed in a humidity oven (Standard Environmental Systems Model RB/5) cycles from 32° C. to 61° C. at plus or minus 5 to 95% relative humidity. The treated panels were also checked daily for adhesion.

A further test to which the coated panels were subjected to was "thermoformability" which was performed on ¼"×4"×10" coated polycarbonate panels and cured for 90 minutes at 135° C. in a vented oven. The coated panels were then subjected to a cold bending to a 25 inch radius and then heated for 1 hour at 138° C.

The following Table shows the results obtained with polycarbonate panels treated with UV-stabilized silicone hardcoat formulations containing 16% by weight of the UV stabilizer, based on the weight of solids, which amounted to 3.2% by weight of the total coating composition, where "QUV Aging" means the time required to develop microcracks as visually determined by a 10X magnifying lens. Thermoformability was also examined for cracks on both sides, silane ethoxy value, and Humidity Oven Test and Water Soak Test are as previously described:

TABLE IV

| Silane Ethoxy Value | QUV Aging | |
|---|---|---|
| | Microcracks Hours | Adhesive Failure Hours |
| 0.5 | >1700 | >2200 |
| 3 | 750 | 1000 |
| | Humidity Oven Test | |
| 0.5 | Fails adhesion at 32 days | |
| 3 | Fails adhesion at 10 days | |
| | 65° C. Water Soak Test | |
| 0.5 | Fails adhesion after 12 days | |
| 3 | Fails adhesion after 5 days | |
| | Thermoformability | |
| 0.5 | Passes 25 inch radius (no cracks both sides) | |
| 3 | Fails | |

The above results show that the UV-absorbing agent of the present invention, as shown by formula (4), provides superior UV-stabilized silicone hardcoat formulations, as well as coated substrates treated with such formulations as compared prior art to UV absorbing agents, UV-stabilized silicone hardcoat formulations containing such prior art UV-absorbing agents and coated substrates treated with such prior art UV-stabilized silicone hardcoat formulations.

It was further found that the UV-absorbing agents of the present invention as shown by formula (4), could be incorporated into silicone hardcoat formulations at up to 40% by weight, based on the weight of the total solids in the silicone hardcoat formulation, without significantly altering the appearance of air dried or cured coatings obtained by coating thermoplastic substrates in accordance with the practice of the present invention. The percent change in haze after 300 cycles with the Taber Abrasion Tester also was not significantly affected. In addition, valuable results also were obtained when the UV-absorbing agent of formula (4) at levels of up to 25% by weight, based on the weight of silicone hardcoat formulation solids was combined with various antioxidants, such as Tinuvin 765, of the Ciba Geigy Company.

Although the above examples are directed to only a few of the very many variables of the UV-absorbing agents, UV silicon hardcoat formulations containing such UV-absorbing agents and thermoplastic substrates coated with such UV stabilized silicone hardcoat formulations of the present invention, the present invention further includes other UV-absorbing agents as shown by Formula (4) and mixtures thereof and combinations of such UV-absorbing agents with other silicone hardcoat formulations containing colloidal silica and cohydrolyzed silane of formula (2) and various thermoplastic substrates, for example, Ultem polyetherimide, Valox polyester, etc., which may be optionally primed with an acrylic primer. For example, the aforementioned thermoplastic substrate can be primed with a thermosetting acrylic emulsion, such as Rohm & Haas 4% Rhoplex which can contain UV absorbers of the present invention and other UV absorbers such as substituted-hydroxybenzophenones, etc., and optionally combinations thereof with antioxidants, etc., which are useful in a variety of applications, such as glazing materials, headlamps, automotive wheel covers, etc.

What I claim as new and desire to secure by Letters Patent of the United States is:

1. An ultraviolet light absorbing agent having the formula,

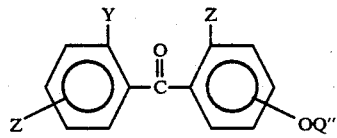

where Q″ is

R is alkyl or alkanoyl having 2 to 6 carbon atoms, Y is H or OH, Z is H, OH, OQ″ or OW, where at least one Z is OH in the ortho position to the carbonyl if Y is H, W is $C_mH_{2m+1}$, m is 1 to 18, n=0, 1 or 2, and "a" has a value of from about 0.5 to about 2.5 inclusive.

2. An ultraviolet light absorbing agent having the formula,

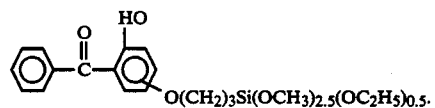

3. An ultraviolet light absorbing agent having the formula,

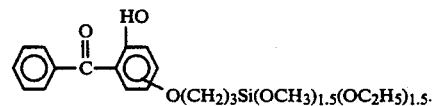

4. An ultraviolet light absorbing agent having the formula,

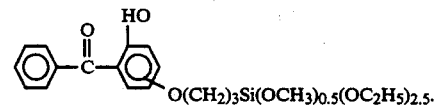

5. A method for making a UV absorbing agent of the formula, which comprises, equilibrating at a temperature of 20° C. to 80° C. a mixture comprising 0.6 to 9 moles of methanol per mole of a trialkoxysilylalkyl ultraviolet light-absorbing agent of the formula,

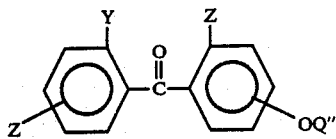

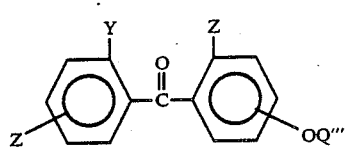

(5)

in the presence of an acid catalyst, where Q″ is

—CH$_2$(CH$_2$)$_n$Si(OCH$_3$)$_{3-a}$(OR)$_a$,

Q‴ is

CH$_2$(CH$_2$)$_n$Si(OR)$_3$

R is alkyl or alkanoyl having 2 to 6 carbon atoms, Y is H or OH, Z is H, OH, OQ″ or OW, where at least one Z is OH in the ortho position to the carbonyl if Y is H, W is C$_m$H$_{2m+1}$, m is 1 to 18, n=0, 1 or 2, and "a" has a value of from about 0.5 to about 2.5 inclusive.

6. A method in accordance with claim 5, where Q″ is CH$_2$(CH$_2$)$_n$Si(OCH$_3$)$_3$-a(OC$_2$H$_5$)$_a$ and n and a are as previously defined.

* * * * *